(12) United States Patent
Padmini et al.

(10) Patent No.: US 7,763,459 B2
(45) Date of Patent: Jul. 27, 2010

(54) CHEMICAL TREATMENT FOR REMOVING CELLULAR AND NUCLEAR MATERIAL FROM NATURALLY OCCURRING EXTRACELLULAR MATRIX-BASED BIOMATERIALS

(75) Inventors: Rangamani Padmini, New York, NY (US); Janine Orban, Warsaw, IN (US); Prasanna Malaviya, Fort Wayne, IN (US)

(73) Assignee: DePuy Spine, Inc., Raynham, MA (US)

( * ) Notice: Subject to any disclaimer, the term of this patent is extended or adjusted under 35 U.S.C. 154(b) by 393 days.

(21) Appl. No.: 10/954,971

(22) Filed: Sep. 30, 2004

(65) Prior Publication Data

US 2005/0260612 A1 Nov. 24, 2005

Related U.S. Application Data

(60) Provisional application No. 60/508,007, filed on Oct. 2, 2003.

(51) Int. Cl.
*C12P 1/00* (2006.01)
*C12P 5/02* (2006.01)

(52) U.S. Cl. .................. 435/325; 435/41; 424/93.7; 424/423

(58) Field of Classification Search .............. 424/93.7, 424/423; 435/325, 41
See application file for complete search history.

(56) References Cited

U.S. PATENT DOCUMENTS

| | | | |
|---|---|---|---|
| 5,507,810 A | 4/1996 | Prewett et al. | |
| 5,711,969 A | 1/1998 | Patel et al. | |
| 5,755,791 A | 5/1998 | Whitson et al. | |
| 5,855,619 A | 1/1999 | Caplan et al. | |
| 5,955,110 A | 9/1999 | Patel et al. | |
| 5,968,096 A | 10/1999 | Whitson et al. | |
| 5,993,844 A | 11/1999 | Abraham et al. | |
| 5,997,575 A | 12/1999 | Whitson et al. | |
| 6,206,931 B1 | 3/2001 | Cook et al. | |
| 6,371,992 B1 | 4/2002 | Tanagho et al. | |
| 6,376,244 B1 * | 4/2002 | Atala | ................ 435/376 |
| 6,482,584 B1 | 11/2002 | Mills et al. | |
| 6,485,723 B1 | 11/2002 | Badylak et al. | |
| 6,545,042 B2 | 4/2003 | Sung et al. | |
| 6,572,650 B1 | 6/2003 | Abraham et al. | |
| 6,599,690 B1 | 7/2003 | Abraham et al. | |
| 7,087,089 B2 * | 8/2006 | Patel et al. | ................ 623/23.72 |
| 2003/0026787 A1* | 2/2003 | Fearnot et al. | ............. 424/93.7 |
| 2004/0078076 A1 | 4/2004 | Badylak et al. | |
| 2007/0250177 A1 | 10/2007 | Bilbo | |

OTHER PUBLICATIONS

Janis, A et al., "The Effects of Chemical Removal of Nucleic Acids on the Mechanical Properties of Porcine Small Intestinal Submucosa," Society for Biomaterials 29$^{th}$ Annual Meeting, pp. 272, 2003.

Kathleen A. Derwin, Andrew R. Baker, Rebecca K. Spragg, Diane R. Leigh and Joseph P. Iannotti, "Commercial Extracellular Matrix Scaffolds for Rotator Cuff Tendon Repair, Biomechanical, Biochemical and Cellular Properties," The Journal of Bone & Joint Surgery (JB&JS), *J Bone Joint Surg. am. 2006*; 88:26 65-2672. doi: Oct. 21, 2006/JBJS.E.01307.

M.H. Zheng, J. Chen, Y. Kirilak, C. Willers, J. Xu, D. Wood, "Porcine Small Intestine Submucosa (SIS) Is Not an Acellular Collagenous Matrix and Contains Porcine DNA: Possible Implications in Human Implantation," *Wiley InterScience* (www.interscience.wiley.com) Published online Feb. 25, 2005.

Abraham, G. et al., "Evaluation of the porcine Intestinal Collagen Layer as a Biomaterial," J. Biomed. Mater. Res. 51:442-452 (2000).

Biological Effects of Ultrasound; Mechanisms and Clinical Implications, National Council on Radiation Protection and Measurements (NCRP) Report No. 74, NCRP Scientific Committee No. 66: Wesley L. Nyborg, chairman; NCRP, Bethesda, MD (1983).

Freshney, Culture of Animal Cells. A Manual of Basic Technique, 2d ed., A.R. Liss, Inc., N. Y., Ch. 9, pp. 107-126 (1987).

Goleckner, D.C. et al., "Mechanical Evaluation and Design of a Multilayered Collagenous Repair Biomaterial," J. Biomed. Mater. Res. 52:365-73 (2000).

Stadtman, E. et al., "Fenton Chemistry Amino Acid Oxidation," J. Biol. Chem. 266:17201-211 (1991).

Whitson, B.A. et al., "Multilanninate Resorbable Biomedical Device Under Biaxial Loading," J. Biomed. Mater. Res. 43:277-81 (1998).

* cited by examiner

*Primary Examiner*—Ruth A Davis
(74) *Attorney, Agent, or Firm*—Nutter McClennen & Fish LLP

(57) ABSTRACT

A method is provided for sequential decellularization of an isolated tissue using solubilizing solutions comprising at least one oxidizing agent that removes all cellular and nuclear materials from the tissue while substantially maintaining the biological and, mechanical properties, and the biochemical properties of the resulting extracellular matrix.

24 Claims, 9 Drawing Sheets

A

B

CHEMICAL TREATMENT FOR REMOVING CELLULAR AND NUCLEAR MATERIAL FROM NATURALLY OCCURRING EXTRACELLULAR MATRIX-BASED BIOMATERIALS

This application claims the benefit of priority of U.S. Ser. No. 60/508,007, filed Oct. 2, 2003 entitled "Chemical Treatment for Removing Cellular and Nuclear Material from Naturally Occurring Extracellular Maxtrix-Based Biomaterials," the teachings of which are incorporated herein by reference.

BACKGROUND OF THE INVENTION

The technical field of this invention relates to methods of decellularizing a tissue. In particular, decellularizing a tissue by chemically treating the isolated tissue with a series of oxidizing agents that remove the cellular and nuclear material from the isolated tissue while substantially retaining the biological and mechanical properties, as well as the biochemical composition of the resulting ECM.

Naturally occurring extracellular matrix (ECM)-based biomaterials are used for tissue repair and regeneration. One such extracellular matrix is small intestine submucosa (SIS). SIS has been used to repair, support, and stabilize a wide variety of anatomical defects and traumatic injuries. Commercially available SIS material is derived from porcine small intestinal submucosa that remodels to the qualities of its host when implanted in human soft tissues. Further, it is taught that the SIS material provides a natural matrix with a three-dimensional microstructure and biochemical composition that facilitates host cell proliferation and supports tissue remodeling. Indeed, SIS has been shown to contain biological molecules, such as growth factors and glycosaminoglycans that aid in the repair of soft tissue of the human body. The SIS material currently being used in the orthopedic field is provided in a dried and layered configuration in the form of a multilaminate patch. Several preclinical and clinical research studies have used laminated SIS to repair or regenerate soft tissue such as tendons (rotator cuff tendons, Achilles tendon, patellar tendon, flexor tendons etc.), ligaments (anterior and posterior cruciate ligaments, medial and lateral co-lateral ligaments), fibrocartilage (meniscus, labrum) and cartilage.

To date, some commercially produced ECM while useful for tissue regeneration, may still retain residual non-viable nucleic acids. These non-viable nucleic acids may leach into the surrounding environment during tissue regeneration. Although a number of different techniques have been employed to treat the ECM, few have successfully removed all of the residual nucleic acids without compromising mechanical, biological, and/or the the biochemical properties of the ECM.

Some studies have shown that remnants of degraded DNA are still present within the ECM after a cleaning and disinfecting process using a series of ethanol and peracetic acid washes. Some of the treatment methods also use chemicals which are difficult to wash out of the tissue (e.g., detergents), resulting in a high residual content of the chemical in the ECM, thus compromising its biocompatibility. Other methods using a combination of acids, bases and chelating agents, remove the proteoglycans and other non-collagenous proteins from the material (Janis, et al., (2003) *Society for Biomaterials 29th Annual Meeting transactions*, p. 272). Thus, these treatments remove the cellular remnants, but their effect on the mechanical properties of the material is usually detrimental.

U.S. Pat. No. 5,993,844 discloses a method for complete removal of nucleic acids from tissue to create an acellular matrix material that can be used as a biomaterial for tissue engineering or tissue repair purposes. However, the process disclosed in this patent calls for treatment of the ECM biomaterial with harsh bases like sodium hydroxide (NaOH), and/or acids like hydrogen chloride (HCl) in addition to treatment with chelating agents like EDTA. Such treatment leads to removal of nearly all nuclear material from the ECM, but at the same time also significantly removes non-collagenous material from the ECM biomaterial. While this may be desirable in some applications, other applications may require preservation of at least some of the non-collagenous components of tissue (e.g., growth factors, glycoproteins, glycosaminoglycans, etc.) to retain some of the biological properties of the material. Further, it has been documented that treatment with such harsh chemicals significantly compromises the mechanical properties of the ECM biomaterial (Janis et al., (2003) Supra), frequently requiring a chemical cross-linking step subsequent to the nuclear material removal step to strengthen the ECM biomaterial (Abraham et al., (2000) *J Biomed Mater Res*, 51:442-4552; Goleckner et al., (2000) *J Biomed Mater Res.* 52:365-373).

Therefore, there is a need for a treatment protocol that is effective in removing residual nucleic acids from an ECM without significantly altering the mechanical and biological properties, or the biochemical composition of the ECM biomaterial.

SUMMARY OF THE INVENTION

The invention is based on the discovery that cellular and nuclear material can be removed from a tissue with a series of extraction steps using solubulizing fluids comprising at least one decellularizing agent, such as an oxidizing agent. The extraction steps are designed to remove cellular and nuclear components from the tissue while retaining the native biological and mechanical properties, as well as the biochemical composition of the resulting ECM. The method of the invention avoids the use of chemicals that can potentially compromise the mechanical strength and biochemical composition of the ECM. These treated ECMs can be used for tissue regeneration in preparing implants for treating or healing injured or diseased joints.

Accordingly, in one aspect, the invention pertains to a method of decellularizing a tissue by sequential extraction, comprising treating the isolated tissue with a first solubilizing fluid comprising at least one oxidizing agent at a concentration effective to extract cellular and nuclear material from the tissue while maintaining the biochemical composition of the tissue. The isolated tissue is then treated with a second solubilizing fluid comprising at least one oxidizing agent, to further remove cellular and nuclear material while maintaining the biochemical composition of the tissue. After the treatment step, the isolated tissue is washed in a washing fluid to remove cellular debris while maintaining the biochemical composition of the tissue until the isolated tissue is substantially free of cellular and nuclear material.

In another aspect, the invention pertains to a method for producing a decellularized small intestinal submucosa by sequential extraction comprising treating the isolated small intestinal submucosa with a first solubilizing fluid comprising at least one oxidizing agent at a concentration effective to extract cellular and nuclear material from the small intestinal submucosa while maintaining the biochemical composition of the tissue. The isolated small intestinal submucosa is then treated with a second solubilizing fluid comprising at least one oxidizing agent, to further remove cellular and nuclear material while maintaining the biochemical composition of the small intestinal submucosa. After the treatment steps, the isolated small intestinal submucosa is washed in a washing fluid to remove cellular debris while maintaining the biochemical composition of the tissue until the isolated tissue is substantially free of cellular and nuclear material.

In yet another aspect, the invention pertains to a biocompatible tissue implant, comprising a network of extracellular matrix (ECM) derived from submucosa treated with a first solubilizing fluid comprising at least one oxidizing agent at a concentration effective to extract cellular and nuclear material while substantially maintaining the biochemical composition and the mechanical and biological properties of the tissue, and a second solubilizing fluid comprising at least one oxidizing agent, to further remove cellular and nuclear material while substantially maintaining the biochemical composition and the mechanical and biological properties of the small intestinal submucosa, and a washing fluid to remove cellular debris, wherein the matrix consists of a framework of collagen substantially free of cellular material and viable and non-viable nucleic acids, and wherein the matrix is effective to permit the growth of cells.

DETAILED DESCRIPTION OF THE INVENTION

Figure 1:
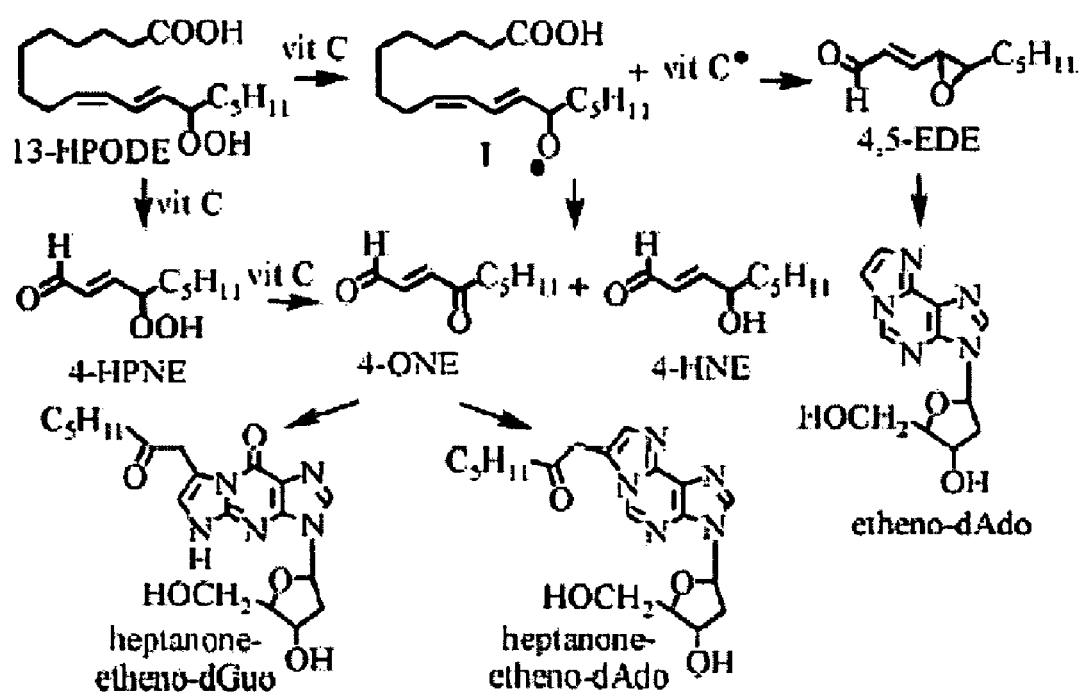
FIG. 1 a schematic drawing showing the chemistry of ascorbate radical anion and formation of adducts.

So that the invention may more readily be understood, certain terms are first defined as follows:

The terms "ECM" or "extracellular matrix" as used herein refer to the non-cellular tissue material present within all types of submucosa tissue. Any tissue, including submucosa tissue, has two parts: the parenchyma (i.e., the cellular part) and the stroma (i.e., the tissue material external to the cells). Submucosa used to generate ECM's can be derived from a number of sources that include, but are not limited to naturally occurring small intestine, liver basement membrane, stomach, bladder, alimentary, respiratory, and genital submucosa. In addition, the submucosa can be derived from any mammalian subject such as bovine, porcine, ovine, etc. The ECM can be cross-linked e.g., via the collagen in the ECM, and used to form other structures such as foams. It is not within the definition of a naturally occurring ECM to alter, extract or separate and purify the natural biochemical components or subcomponents (e.g., collagen or growth factor) and reform a matrix material from these extracted and purified components or subcomponents. It is also not within the definition of a naturally occuring ECM to obtain an extracellular matrix by culturing cells in vitro, inducing them to secrete a layer or layers of extracellular matrix in vitro, and then decellularize the matrix to produce an acellular ECM.

The term "decellularized tissue" as used herein refers to a tissue from which a substantial amount of cellular and nucleic acid content has been removed leaving behind a complex interstitial structure of extracellular matrix (ECM) that can be used as a scaffold for tissue regeneration. Tissues are composed of various specialized tissue structures. The specialized tissue structures of a tissue are the parenchyma tissue, and they provide the specific function associated with the tissue. Most tissues also have a framework composed of unspecialized connective tissue which supports the parenchyma tissue. The process of decellularization removes the parenchyma tissue, leaving behind the three-dimensional interstitial structure of connective tissue, primarily composed of collagen and other extracellular proteins, glycoproteins, and proteoglycans. The interstitial structure provides the supportive framework that allows cells to attach to, and grow on it. The decellularization treatment is designed such that the cellular and nuclear material, as well as residual viable, and/or non-viable nucleic acids, are removed without substantially affecting the biological and mechanical properties or the biochemical composition of the ECM. Thus, the treatment process retains within the ECM the essential factors required for cell growth and proliferation, such as growth factor, glycosaminoglycan, etc.

The terms "decellularized extracellular matrix" or "decellularized ECM" as used herein refers to extracellular matrix material that has been cleaned, disinfected, sterilized, and optionally cross-linked.

The term "isolated tissue" as used herein refers to a tissue that has been removed from a mammal. Suitable mammals include humans, primates, dogs, cats, mice, rats, cows, horses, pigs, goats and sheep. The term "isolated tissue" also refers to a commercially available ECM tissue that requires further modification by removal of viable and/or non-viable nucleic acids.

The term "sequential extraction" as used herein refer to a step-by-step procedure for treating the isolated tissue to remove the cellular and nuclear material from the isolated tissue. For example, the isolated tissue can be treated with a first solubilizing fluid comprising at least one oxidizing agent, such as hydrogen peroxide. After treatment in the first solubilizing agent, the isolated tissue can then treated with a second solubilizing agent that comprises at least one oxidizing agent, such as peracetic acid. It is to be understood that the order in which the isolated tissue is treated can be reversed as long as each treatment step remains separate. That is to say, the first step of the extraction process may involve treating the isolated tissue with the second solubilizing fluid, and the second step of the extraction process may involve treating the isolated tissue with the first solubilizing fluid.

Also within the scope of the invention are treatments that involve more than two sequential extraction steps, for example, a first treatment with a first solubilizing fluid comprising a first oxidizing agent (e.g., peracetic acid), followed by a second treatment with a second solubilizing fluid comprising a second oxidizing agent (e.g., hydrogen peroxide), followed by a third treatment with a third solubilizing fluid comprising a third oxidizing agent (e.g., performic acid), and so forth, as long as each extraction step substantially retains the biocompatible, biological, and mechanical properties, as well as the biochemical composition of the ECM.

The term "solubilizing fluid" as used herein refers to a solution into which a decellularizing agent, such as an oxidizing agent, is dissolved to provide a concentration of the oxidizing agent that extracts cellular and nuclear content from the isolated tissue without significantly altering the biological and mechanical properties, or the biochemical composition of the ECM.

The phrase "substantially free" as used herein refers to a ECM produced by the serial extraction process of the invention where at least 30% of the viable and non-viable nucleic acids, and cellular material have been removed from the ECM, preferably about 40%, 50%, 60%, 70%, 80%, 90%, 91%, 92%, 93%, 94%, 95%, 96%, 97%, 98%, 99% or 100% of the viable and non-viable nucleic acids, and cellular matierial have been removed. The removal of the nucleic acids from the ECM can be determined by histological examination of the ECM. The removal can also be determined by examining the DNA content in the ECM by a biochemical assay, e.g., PicoGreen® assay or the diphenylamine assay.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

Various aspects of the invention are described in further detail in the following subsections:

I. Agents for Tissue Decellularization

In one aspect, the invention pertains to using decellularizing agents, such as oxidizing agents, to remove cellular and nuclear material from an isolated tissue. The resulting decellularized ECM retains similar biological and mechanical properties, as well as a similar biochemical composition as the native ECM. The decellularized ECM biomaterial can be used for tissue regeneration.

Suitable tissues for decellularization include, but are not limited to, small intestinal submucosa, urinary bladder submucosa, stomach submucosa, uterine submucosa, and liver basement membrane submucosa. In a preferred embodiment, the tissue is small intestinal submucosa. The methods of the invention can also be used to remove residual non-viable nucleic acids from any pretreated commercially available ECM that retains such residual nucleic acids.

Small intestinal submucosa is an acellular, collagen-based bioactive matrix that is used extensively as a scaffold for tissue engineering therapies and also for the preparation of implants for human subjects. Before small intestinal submucosa implants are prepared, the material must be cleaned and disinfected, and decellularized to remove cellular components embedded in the tissue.

Decellularizing agents that can be used in the methods of the invention are those agents that are effective in removing cellular and nuclear material from the isolated tissue without substantially compromising the biocompatible, biological and mechanical properties, or the biochemical composition of the ECM. Examples of decellularizing agents that can be used for decellularization of the tissue include, but are not limited to, oxidizing agents (e.g., hydrogen peroxide, peroxy acids), ascorbic acid (vitamin C), chelating agents (e.g., EDTA, EGTA), methionine, cysteine, maleic acid, and polymers that bind to DNA (e.g., Poly-L-lysine, polyethylimine (PEI) and polyamidoamine (PAMAM)).

In one embodiment, the decellularizing agent is an oxidizing agent that generates a reactive hydroxyl radical (OH.) or a reactive oxygen species (e.g., $O_2^-$) that interacts with a nucleic acid (e.g., DNA). Examples of oxidizing agents that produce reactive hydroxyl ions include, but are not limited to hydrogen peroxide, benzoyl peroxide, and t-butyl hydroperoxide. The hydroxyl radical being highly reactive can attack membrane lipids, DNA, and other essential cell components. Transition metals catalyze the formation of hydroxyl radical and thereby increase the efficacy of hydrogen peroxide. Many metal ions are inherently present within cells, therefore DNA damage by hydroxyl radicals is pronounced with the addition of hydrogen peroxide.

Reactive oxygen species cause a spectrum of DNA lesions, including single strand breaks, double strand breaks, crosslinking of DNA and damage to bases and the deoxyribose moiety. These species have moderate reactivity in aqueous solutions, and their conversion to the highly reactive OH. is responsible for the DNA damage. The mode of action for DNA damage by the hydroxyl free radical is by Fenton chemistry (Stadtman, et al., (1991) *Fenton Chemistry, J. Biol. Chem.*, Volume: 266:17201).

In other embodiments, the decellularizing agent is a chemical that binds to, and modifies DNA, such as ascorbic acid (vitamin C), methionine, cysteine and maleic acid. Ascorbic acid, methionine and cysteine are relatively harmless to the collagen framework in the isolated tissue. Ascorbate forms a radical anion that forms adducts with the bases in DNA. The postulated chemistry is illustrated in FIG. 1.

The decellularizing agents are used in a solubilizing fluid (e.g., distilled water, reverse osmosis water, or physiological buffer) having a pH of about 1.0 to about 14, more preferably pH of about 2.0 to about 10, a pH of about 2.0 to about 8.0, a pH of about 2 to about 6, and most preferably a pH of about 2 to about 4. In methods of the present invention, the extraction process will generally be conducted under conditions, and for a period of time which provide the recovery of characteristic submucosa ECM that are substantially free from residual nucleic acids. In this regard, desirable processes of the invention involves immersing the tissue (e.g., by submersing or showering) in solubilizing fluid comprising at least one decellularizing agent such as an oxidizing agent (e.g., hydrogen peroxide or peracetic acid) for a period of about 5 minutes to about 40 hours, and more preferably, for about 0.5 hours to about 5 hours and most preferably, for about 1 hour to about 2 hours. In one embodiment, a first solubilizing fluid comprises an oxidizing agent such as hydrogen peroxide and the second solubilizing fluid comprises an oxidizing agent such as peracetic acid. In another embodiment, the first solubilizing fluid comprises an oxidizing agent such as peracetic acid and the second solubilizing fluid comprises an oxidizing agent such as hydrogen peroxide.

The concentration of the oxidizing agent in the solubilizing fluid will depend on which oxidizing agent is being used for the decellularization process. The concentration of the oxidizing agent is selected to be a concentration that is effective in removing cellular and nuclear content from the isolated tissue without substantially affecting the biocompatible, biological, mechanical properties, or the biochemical composition of the resulting ECM. For example, the concentration of hydrogen peroxide in the solubilizing fluid can range from about 1% to 30% by volume. More preferably the hydrogen peroxide concentration is from about 1% to 20% by volume. Even more preferably the hydrogen peroxide concentration is from about 1% to 5% by volume, and most preferably 3% by volume. The solubilizing fluid may or may not be buffered to a pH from about 5 to 9. More preferably the pH is from about 6 to 7.5. These concentrations can be diluted in distilled water or alcohol. Most preferably the alcohol is ethanol. The solubilizing fluid temperature can range from about 4 to 40° C. More preferably the solubilizing fluid temperature is from about 10 to 30° C. Most preferably, the solubilizing fluid temperature is from about 22 to 25° C. The treatment time can range from about 1 to 400 minutes. Preferably, the treatment time is from about 120 to 240 minutes. More preferably, the treatment time is from 180 to 210 minutes.

Another oxidizing agent is a peroxy acid. Examples of peroxy acids include, but are not limited to, peracetic acid (also known as peroxyacetic acid and acetyl hydroperoxide), perpropionic acid, perbenzoic acid, performic acid, diperoxyphthalic acid, or peroxyhexanoic acid. Peracetic acid is the most preferred peroxy acid. The peracetic acid can be dissolved in C6 or a lower ethanol. The peracetic acid is preferably diluted into about a 2% to about 50% by volume alcohol solution. The concentration of the peracetic acid may range, for example, from about 0.05% by volume to about 2.0% by volume. Most preferably the concentration of the peracetic acid is from about 0.1% to about 0.3% by volume.

An exemplary preparative processes, the decellularizing agents may be dissolved in a dilute aqueous alcohol solution, where the alcohol preferably has from 1 to about 6 carbon atoms. More preferred alcohols for use in the invention are selected from the group consisting of ethanols, propanols and butanols. Ethanol is a particularly useful alcohol for these purposes.

In another embodiment, the decellularizing agent is a non-organic carboxylic acid, such as a Brönsted acid (e.g., ascorbic acid). Chelating agents such as EDTA, EGTA may also be used as agents for decellularization. Chelating agents act with heavy metal ions to bind the DNA and remove it from the matrix. Polymers used in gene transfection, such as Poly-L-lysine, polyethylimine (PEI) and polyamidoamine (PAMAM) may also be used for decellularization of isolated tissues. These cationic polymers that form the DNA-polymer complexes interact electrostatically with the phosphates on DNA to form a compact particle.

Also within the scope of the invention are solubilizing fluids that comprise a combination of decellularizing agents to decellularize an isolated tissue, e.g., a combination of ascorbic acid and methionine. The solublizing fluid may also comprise combinations comprising at least one oxidizing agent with at least one other decellularizing agent such as chelating agents. Combinations of decellularizing agents used in a solubilizing fluid are those that substantially remove cellular and nuclear material from the tissue, and in particular remove residual nucleic acids without substantially affecting the biochemical and mechanical properties of the ECM. Thus, the ECM retains its native biological, mechanical, and biochemical properties.

II. Isolation of Natural Tissue

A tissue can be isolated from the subject, for example, a diseased tissue in a subject can be removed and decellularized, as long as the disease does not harm the connective tissue, e.g., due to tissue necrosis. The decellularized tissue can be used as a three-dimensional scaffold to reconstruct an artificial tissue. An allogenic artificial tissue can be reconstructed using the subject's own decellularized tissue as a scaffold and using a population of cells derived from the subject's own tissue.

A xenogenic artificial tissue can be reconstructed using the subject's own decellularized tissue as a scaffold, and using cell populations derived from a mammalian species that are different from the subject. For example the different cell populations can be derived from mammals such as primates, dogs, cats, mice, rats, cows, horses, pigs, goats and sheep.

A tissue can also be derived from a human cadaver, or from mammalian species that are different from the subject, such as tissue from primates, dogs, cats, mice, rats, cows, horses, pigs, goats and sheep. Standard methods for isolation of a target tissue are well known to the skilled artisan and can be used to isolate the tissue. In a preferred embodiment, the tissue is porcine small intestine submucosa (SIS). Alternatively, the tissue (e.g., SIS), may also be purchased commercially from any sausage casing company (e.g., Excel Corporation, Inc., a subsidiary of Cargill Foods, Inc.).

III. Decellularization of Tissue

An isolated tissue can be decellularized by removing the entire cellular and nuclear material from the tissue, as described in the Examples section. The decellularization process comprises a series of sequential extractions. One feature of this extraction process is that harsh extraction, that may disturb or destroy the biological, mechanical, and in particular, biochemical properties of the ECM, be avoided. Thus, the extraction process should result in a decellularized ECM that retains similar biochemical and mechanical properties as the native ECM.

The decellularization method requires the sequential removal of components of the isolated tissue. The first step involves mechanically agitating the isolated tissue in a first solubilizing fluid comprising a first oxidizing agent (e.g., hydrogen peroxide), until the native cellular content, such as nuclear and cytoplasmic components of the tissue have been removed. During this step, the cellular material of the isolated tissue is solubilized without dissolving the ECM, or without affecting the native properties of the ECM. That is to say that the chemical treatment removes the cellular and nuclear content but retains the biochemical and mechanical properties of the native ECM (e.g., retains factors that are required for growth and proliferation of cells, such as growth factors and glycosaminoglycans, etc). The step can also be used to remove residual non-viable nucleic acids that remain in ECM that have already been treated to remove cellular and nuclear material, e.g., commercially available ECMs.

After the first treatment step, the isolated tissue is treated with a second solubilizing fluid comprising a second oxidizing agent (e.g., peracetic acid), that further removes cellular and nuclear components from the isolated tissue. The next step in the sequential extraction may involve further treatments of the isolated tissue with other solubilizing fluids comprising at least one oxidizing agent. After the final treatment step, the next step in the sequential extraction involves removal of the solubilized components by mechanically agitating the isolated tissue in a washing fluid. Removal of the cytoplasmic and nuclear components leaves behind a decellularized ECM that has substantially the same properties as the native ECM.

After removing the solubilized cytoplasmic and nuclear components, the next step of the sequential extraction may involve equilibrating the decellularized tissue in an equilibrating fluid. Examples of an equilibrating fluid include, but are not limited to, distilled water, water obtained via reversed osmosis process, physiological buffer and culture medium.

The decellularized tissue may be dried for long term storage. Methods for drying the decellularized tissue include, but are not limited to, freeze-drying or lyophilizing the tissue to remove residual fluid. The lyophilized decellularized tissue can be stored at a suitable temperature until required for use. The tissue may also be dried in a vacuum bed (vacuum drying). Prior to use, the decellularized tissue can be equilibrated in suitable physiological buffer or cell culture medium. Examples of suitable buffers and culture media are described.

The tissue can be decellularized using gentle mechanical agitation methods that are sufficient to help remove the cellular and nuclear material. However, the mechanical agitation methods should not damage or destroy the ECM. In one embodiment, the mechanical agitation method involves using a magnetic stir plate and a paddle, e.g., a magnetic stirrer. The isolated tissue is placed in a container with a suitable volume of fluid and stirred on the magnetic stir plate at a suitable speed. A suitable speed for stirring the isolated tissue will depend on the size of the isolated tissue. For example, rotation at about 50 revolutions per minute (rpm) to about 150 rpm. A larger sized tissue sample will require a faster speed, compared with smaller sample sizes. The volume of fluid in which the isolated tissue is placed in will also depend on the size of the isolated tissue.

In another embodiment, the mechanical agitation method involves using a mechanical rotator. The tissue is placed in a sealed container with a suitable volume of fluid. The container is placed on the rotator platform and rotated over 360°. The speed of rotation, and the volume of fluid will depend on the size of the isolated tissue.

In another embodiment, the mechanical agitation method involves using a low profile roller. The tissue is placed in a sealed container with a suitable volume of fluid. The container is placed on the roller platform and rolled at a selected speed in a suitable volume of fluid depending on the size of the tissue. One skilled in the art will appreciate that these mechanical agitation devices can be commercially obtained from, for example, Sigma Co.

In other embodiments, the agitation technique can also include placing the isolated tissue in a closed container e.g., a self-sealing polyethylene bag, a plastic beaker. The container can be placed in a sonicating waterbath, and exposed to sonication methods that include, but are not limited to, acoustic horns, piezo-electric crystals, or any other method of generating stable sound waves, for example, with sonication probes. The sonication should be conducted at a frequency that selectively removes cellular and nuclear material without destroying the interstitial structure. Suitable sonication frequencies will depend on the size and the type of the isolated tissue being decellularized. Typical sonicaton frequencies are between 40 kHz to 50 kHz. However, a fairly wide range of frequencies from subaudio to ultrasound (between about 7 Hz and 40 MHz, preferably between 7 Hz and 20 MHz) would be expected to give sound-enhanced tissue dissociation. Variations in the type of sonication are also contemplated in the invention and include pulsing versus continuous sonication. Power levels for sonication source is between $10^{-4}$ and about 10 watts/cm$^2$ (See Biological Effects of Ultrasound: Mechanisms and Clinical Implications, National Council on Radiation Protection and Measurements (NCRP) Report No. 74, NCRP Scientific Committee No. 66: Wesley L. Nyborg, chairman; 1983; NCRP, Bethesda, Md.).

The mechanical properties of the decellularized tissue can be tested using a number of known techniques such as a mechanical ball-burst test as described in the examples section. This involves preparing mechanically isotropic laminate device about ten layers thick using the treated ECM. An isotropic laminate device is produced by layering two layers of SIS along the longitudinal axis of the tissue, turning the plate on which the layers are being assembled by 72 degrees and laying down the next two layers, turning another 72 degrees, and so on until a 10-layered device is produced. (See e.g., U.S. Pat. Nos. 5,997,575; 5,968,096; 5,955,110; 5,855, 619; 5,755,791; and 5,711,969, incorporated herein by reference.) The laminated device can be dried flat in a vacuum bed to obtain a device which is about 1 mm thick. A cutting template can be used to obtain a 2.5 inch diameter circular disk. The devices are packaged in aluminum foil pouches under vacuum after a nitrogen flush and sterilization via electron beam radiation. The electron beam dose will be 20 kGy +/−10% (Titan Scan, Inc., Lima, Ohio).

For testing the mechanical properties, the devices can be opened from their packages, hydrated in water obtained by reverse osmosis (RO) for 2 minutes, and mounted on a ball burst testing fixture. This fixture clamps the SIS device around it's periphery and pushes a one inch stainless steel ball through the center. The force taken for the ball to burst through the device will be recorded. Preferably, the mechanical forces are in the range of about 30 lbs to 120 lbs, more preferably, about 40 lbs to about 100 lbs, more preferably about 50 lbs to 80 lbs, and even more preferably, about 60 lbs to about 70 lbs.

The biochemical properties can be tested by histological examination of the decellularized ECM, as well as by determining the DNA content in the ECM by biochemical assay such as PicoGreen® assay or the diphenylamine assay. The methods of the invention result in a decellularized ECM that is substantially free from nucleic acids and cellular material. The ECM is at least 30% free of nucleic acid, preferably, 40% free, more preferably about 50%. 60%, 70%, 80%, 90%, and most preferably, 100% free of nucleic acids and cellular material. The content of the viable and non-viable nucleic acids, as measured by PicoGreen® assay, can be in the range of about 50 micrograms/mg to about 0.5 microgram/mg., preferably about 40 micrograms/mg to about 0.4 microgram/mg, preferably about 30 micrograms/mg to about 0.3 microgram/mg, more preferably about 20 micrograms/mg to about 0.2 microgram/mg measured using the PicoGreen® assay, even more preferably about 10 micrograms/mg to about 0.1 microgram/mg measured using the PicoGreen® assay, and most preferably about 35 micrograms/mg to about 3.5 microgram/mg.

The biological properties of the treated ECM can be determined in vivo by comparing the growth of cells (e.g., L929 cells, Rat osteocarcinoma cells, NIH/3T3 fibroblasts, and primary chondroctyes) cultured on the treated ECM with existing commercially available ECMs. The growth and proliferation of the cells can be determined by any number of standardized methods such as microscopy, staining, cell proliferation assays (e.g., MTT assay), and the like.

The biological properties of the treated ECM can also be determined in vivo by examining the formation of scar tissue in an animal model (e.g., rat) in which part of the abdominal wall is removed (1 cm x 1 cm section). In a negative control experiment, the removed section is not replaced with the equivalent size of treated SIS, and results in heavy scaring in this region after two months. In a positive control experiment, the removed section is replaced with the equivalent size of commercially available SIS and show significantly reduced scaring. The treated ECM (e.g., SIS) of the invention can be examined in the same manner for its ability to reduce scarring, and to help regenerate the tissue with the full native architecture and morphology in this region.

IV. Reconstructing Artificial Tissue Using A Decellularized Tissue as a Scaffold.

The invention provides a method of reconstructing an artificial tissue using a decellularized tissue extracellular matrix that is substantially free of viable and non-viable nucleic acid, as a scaffold. This decellularized ECM supports the maturation, differentiation, and segregation of in vitro cultured cell populations to form components of adult tissues analogous to counterparts found in vivo.

The decellularized tissue produced by the method of the invention can be used as a biomaterial scaffold to reconstruct an artificial tissue such as an musculoskeletal tissue, with or without prior in vitro seeding of cells on the biomaterial scaffold. Either allogenic or xenogenic cell populations can be used to reconstruct the artificial tissue. Methods for the isolation and culture of cells are discussed by Freshney, Culture of Animal Cells. A Manual of Basic Technique, 2d Ed., A. R. Liss, Inc., New York, 1987, Ch. 9, pp. 107-126. Cells may be isolated using techniques known to those skilled in the art. For example, the tissue can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, and dispase. Mechanical disruption can also be accomplished by a number of methods including, but not limited to, scraping the surface of the organ, the use of grinders, blenders, sieves, homogenizers, pressure cells, or insonators to name but a few.

Preferred cell types include, but are not limited to, kidney cells, urothelial cells, mesenchymal stem cells bone marrow progenitor cells, smooth or skeletal muscle cells, myocytes (muscle stem cells), fibroblasts, chondrocytes, adipocytes, fibromyoblasts, and ectodermal cells, including dulctile and skin cells, hepatocytes, Islet cells, cells present in the intestine, and other parenchymous cells, osteoblasts and other cells forming bone, ligamanet, tendon, fibrocartilage, or cartilage.

Isolated cells can be cultured in vitro to increase the number of cells available for infusion into the three-dimensional scaffold. The use of allogenic cells, and more preferably autologous cells, is preferred to prevent tissue rejection. However, if an immunological response does occur in the subject after implantation of the reconstructed artificial tissue, the subject may be treated with immunosuppressive agents such as, cyclosporin or FK506, to reduce the likelihood of rejection.

It is important to recreate, in culture, the cellular microenvironment found in vivo for a particular tissue being reconstructed. The invention provides a method in which a decellularized tissue is used as a three-dimensional scaffold to reconstruct an artificial tissue. By using a decellularized tissue that retains the properties of the native tissue (e.g., biochemical and mechanical properties), the decellularized ECM provides an scaffold for cell growth and proliferation which mimics cell growth an proliferation that occurs in vivo. By retaining a three-dimensional interstitial structure that is similar to an in vivo tissue, an optimum environment is created for cell-cell interactions, development and differentiation of cell populations.

The decellularized tissue can be pre-treated with agents prior to perfusion of cultured cells in order to enhance the attachment of cultured cell populations to the decellularized tissue. For example, the decellularized tissue could be treated with collagens, elastic fibers, reticular fibers, glycoproteins, glycosaminoglycans (e.g., hyaluronic acid or its analogs, heparin, heparan sulfate, chondroitin4-sulfate, chondroitin-6-sulfate, dermatan sulfate, keratin sulfate, etc.)

Cultured cell populations can be seeded or perfused into the decellularized tissue. A decellularized tissue perfused with a cell population is referred to as a "perfused tissue." After perfusion of a cell population, the perfused tissue should be incubated in an appropriate nutrient medium. Many commercially available media such as RPMI 1640, Fisher's, Iscove's, McCoy's, Dulbecco's medium, and the like, may be suitable for use. In addition, the culture medium should be changed periodically to remove the used media, depopulate released cells, and add fresh media. During the incubation period, the cells will grow in the perfused tissue to produce a tissue layer.

Additional populations of cultured cells, such as parenchymal cells, can be perfused onto the tissue layer. Parenchyma cells perfused onto the tissue layer can be incubated to allow the cells to adhere to the tissue layer. The parenchyma cells can be cultured in vitro in culture medium to allow the cells to grow and develop until the cells resemble a morphology and structure similar to that of the native tissue. Alternatively, after perfusing the decellularized tissue, the perfused tissue can be implanted in vivo without prior in vitro culturing of the cells.

The methods and compositions of the invention can be used to replace, or repair a structural component in the subject such as ligaments, tendons, cartilage, joints, and bones. The methods and compositions of the invention can be used to create artificial tissue such as kidney, liver, bladder, skin, and the like.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

EXAMPLES

Example 1

Materials and Methods

Materials were obtained commercially as follows: NaOH (Sigma), Methionine (Fluka), Cysteine (Sigma), Ascorbic Acid (Sigma), Hydrogen peroxide (Swan), PAMAM (Sigma), Poly-L-lysine (Sigma), EDTA (Sigma), NaCl (Sigma), Polyethyleneimine (Sigma). Solutions of NaOH, ascorbic acid, cysteine, methionine, EDTA were prepared at a concentration of 0.1 M. PAMAM, poly-1-lysine and polyethyleneimine were prepared in concentrations of 0.5 mg/ml aqueous solutions. Papain (Sigma) digested samples were used for the DNA assays. DNA measurements were done using the PicoGreen® reagent kit as purchased from Molecular Probes. Samples were read on a Biorad Versaflour at an excitation of 480 nm and emission of 520 nm. The PicoGreen® reagent and kit provide a sensitive, one-step, fluorescence-based assay for DNA analysis in solution.

Example 2

Preparation of a Decellularized Tissue

The following method describes the examination of various chemicals for their ability to remove nuclear DNA content from a tissue, such as a small intestinal submucosa (SIS), without substantially affecting the biochemical and mechanical properties of the ECM.

Figure 2:
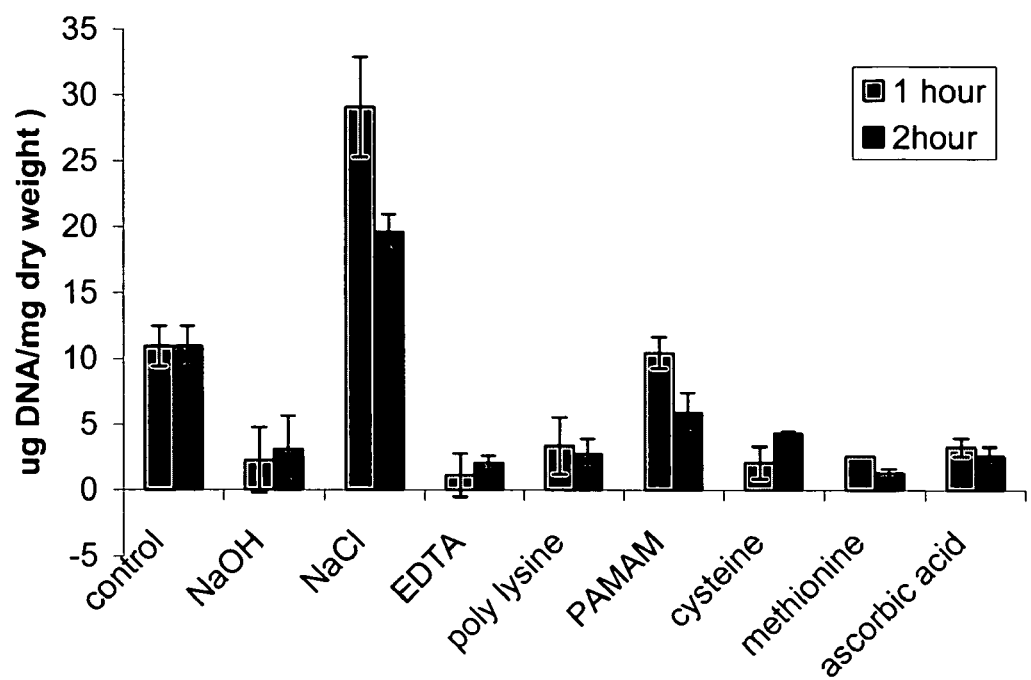
FIG. 2 is a bar graph showing the DNA content after various chemical treatments on SIS trimmings.

The SIS was obtained from a porcine slaughterhouse. Approximately 1 cm length samples of SIS trimmings were treated with solutions of various chemicals as shown in FIG. 2. The different chemicals were selected for their ability to interact with DNA, or their ability to damage DNA. The chemical treatments included incubation of the SIS with 0.1 M concentrations of NaOH, NaCl, EDTA, polylysine, PAMAM, cyteine, methionine, and ascorbic acid. The SIS trimmings were placed in an eppendorf tube comprising 1 ml the chemical, and incubated with the different chemicals at room temperature. The SIS trimmings were removed from the tubes and the amount of DNA in the tissue was measured at 1 hour and 2 hour intervals by PicoGreen® assay. To determine the DNA content, the tissue samples were digested in papain for 18 hours. Any undigested fragments were filtered out and the total protein content was measured using the Lowry assay. The dilution of each of the digested samples was adjusted with distilled water to obtain the same protein concentration in each sample. The DNA content was then measured using the PicoGreen® assay.

The results shown in FIG. 2, demonstrate that NaOH (positive control) significantly reduced the DNA content in the samples, whereas NaCl did not have any effect. The amino acids, cysteine and methionine, also reduced the DNA content in the initial studies. Ascorbic acid also had a significant effect on the SIS samples.

Figure 3:
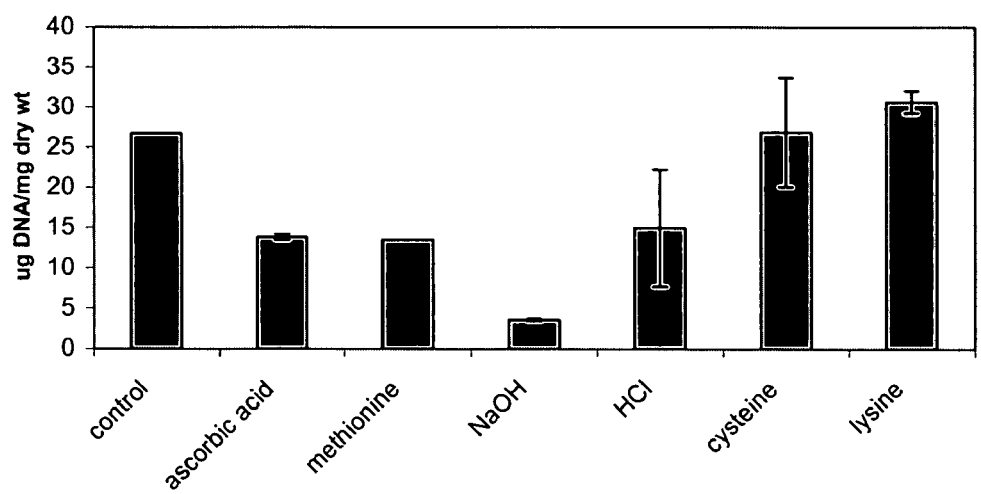
FIG. 3 is a bar graph showing the DNA content after liquid nitrogen treatment.

The process was repeated using a larger number of samples, that helped to narrow down the process to a few treatments which were more effective than others in the removal of residual DNA. The results are shown in FIG. 3. The NaOH and HCl samples were used as positive controls. However, these harsh acids and bases damage and mechanically weaken the ECM. Methionine was also effective, however this amino acid is expensive and not a commercially viable option. The most promising option for the treatment of SIS, based on these studies, was with ascorbic acid.

Example 3

DNA Content after Liquid Nitrogen Treatment

Figure 4:
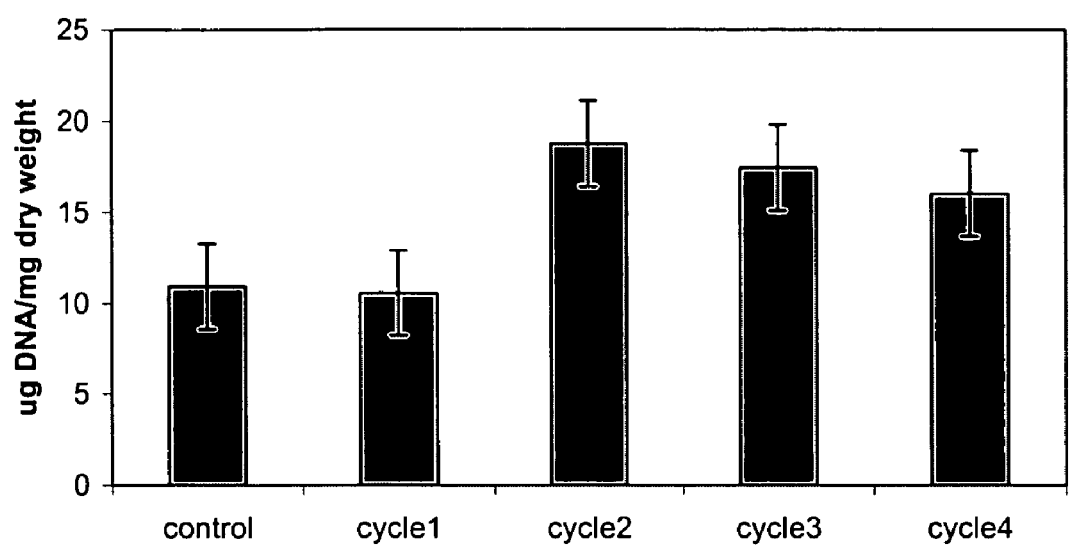
FIG. 4 is a bar graph showing the DNA content after various chemical treatments.

To assess if liquid nitrogen freeze/thaw cycles affected the DNA content within the matrix, 1 cm length SIS trimmings were subject to four different freeze thaw cycles (the cycle involved freezing for one minute, and thawing for a one minute), and measuring the DNA content after each cycle. The results show that even after four repeated cycles, there was no significant reduction in the DNA content, as can be seen from FIG. 4. Thus, the freeze/thaw cycles was not effective in removing residual DNA.

Example 4

Figure 5:
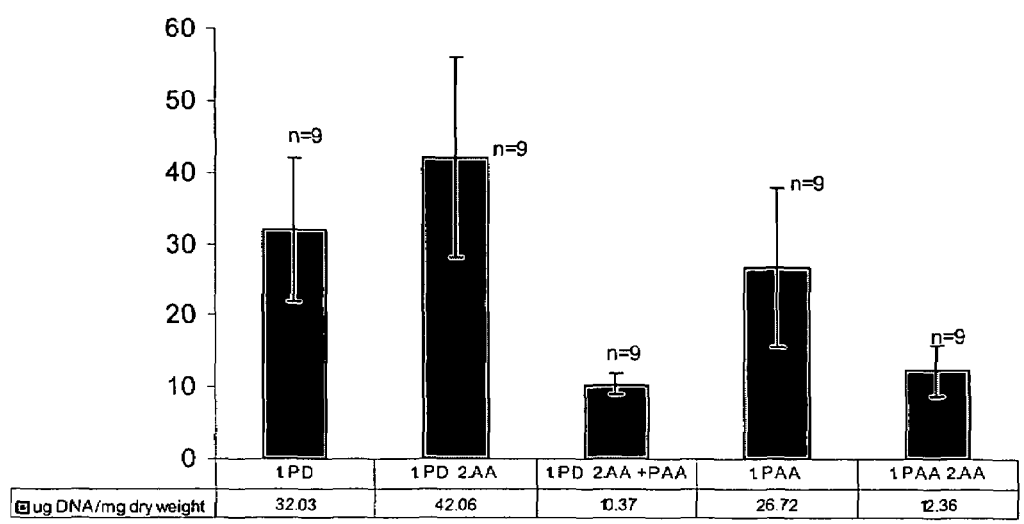
FIG. 5 is a bar graph showing the DNA content in SIS after treatment with ascorbic acid at different processing steps.

DNA Content in SIS after Treatment with Ascorbic Acid at Different Processing Steps To assess the optimum stage at which the tissue should be exposed to ascorbic acid to obtain the maximum removal of DNA, SIS from different stages of processing, both pre- and post disinfected SIS, were tested using a 0.1 M aqueous solution of ascorbic acid. The predisinfected runner was tested in two different ways: (1) ascorbic acid was used before the peracetic acid/ethanol disinfection, (2) the ascorbic acid was mixed with the peracetic acid/ethanol simultaneously. Disinfected runner (already treated with peracetic acid) was also treated with ascorbic acid solution. FIG. 5 shows the effect of the processing step on the DNA content within the ECM matrix. The data shows that DNA was removed with the combination of ascorbic acid and peracetic acid with both pre- and post-disinfected SIS. Combining ascorbic acid treatment with peracetic acid showed a decrease in DNA content in the samples.

Figure 6:
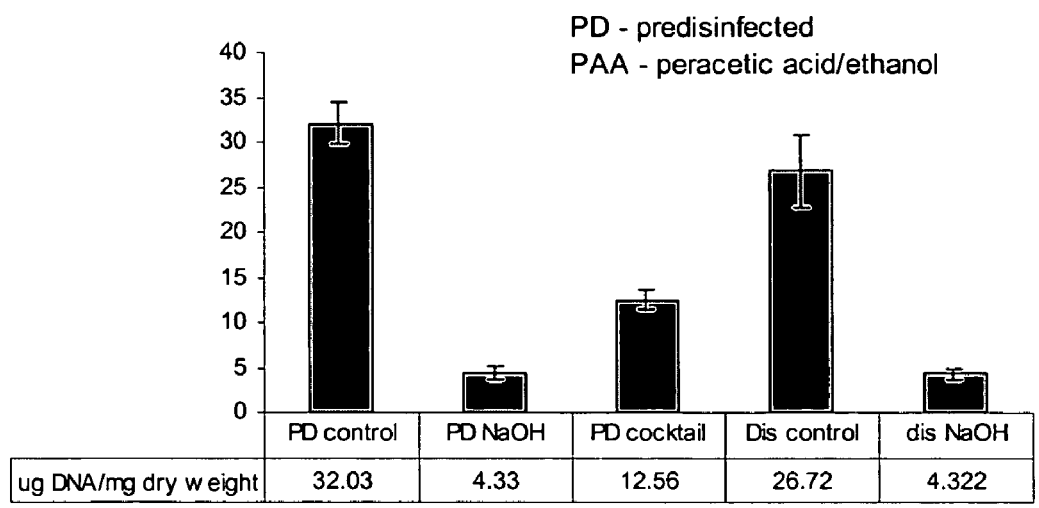
FIG. 6 is a bar graph showing the DNA content after treatment with NaOH at different processing steps.

Since it has been established that NaOH removes almost all of the DNA within the samples, similar tests were run with a 0.1 M NaOH solution as a positive control. FIG. 6 shows the results of DNA content after treatment with NaOH at different processing steps. The data shows that the DNA content after treatment with ascorbic acid was reduced by ~60%, while NaOH removed ~90% of the DNA.

Example 5

DNA Content after Treatment with Hydrogen Peroxide

Although ascorbic acid (vitamin C) is a useful for decellularization, it was unclear whether the residual amounts left in the tissue would effect the properties of the tissue. This lead to the use of hydrogen peroxide, because any residual hydrogen peroxide merely breaks up into water and oxygen and does not adversely effect the tissue.

Figure 7:
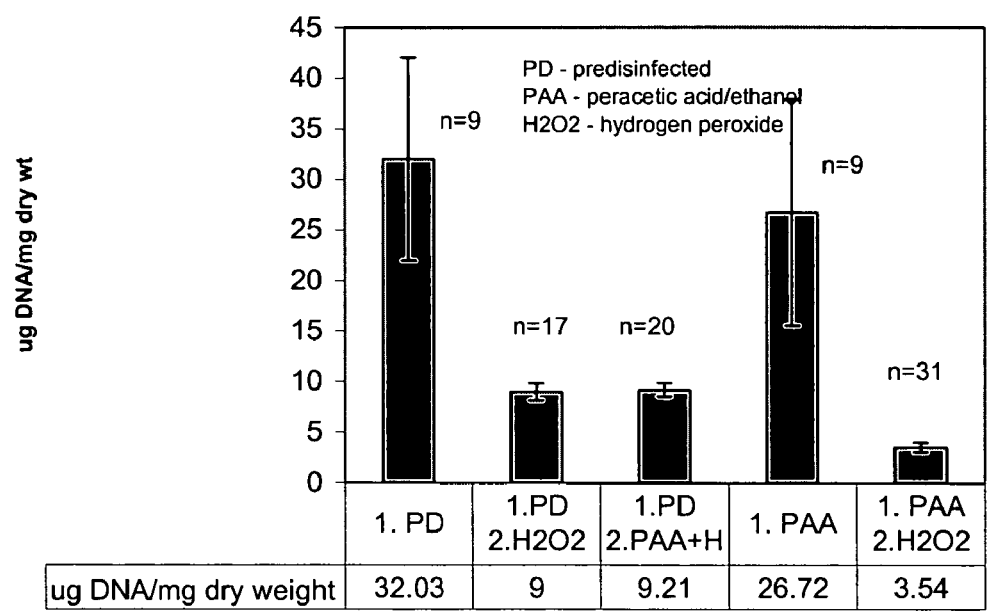
FIG. 7 is a bar graph showing the DNA content after treatment with hydrogen peroxide.

This example shows how the process was optimized to include a wash step that further removes DNA. Based on the chemistry of DNA damage by hydroxyl radicals, it was hypothesized that a chemical treatment that caused DNA removal would not adversely affect the collagen framework of the tissue (mechanical properties would not be adversely affected). Hydrogen peroxide was used as a wash solution of both predisinfected and disinfected samples. The DNA content in the pre-disinfected (PD) samples was lowered by about ~60%, while disinfected SIS was rendered free of ~90% of its nucleic acid content. FIG. 7 shows the DNA content after hydrogen peroxide treatment. The data shows that a combination of peracetic acid and hydrogen peroxide results in a significant removal of DNA.

Removal of the nucleic acid and the cellular debris from the matrix, without negatively affecting its mechanical properties and biocompatibility is essential for the production of implants. Most of the methods described in literature comprise the use of chemicals at basic or acidic pHs. Although these solutions are successful in removing the DNA from the matrix, the mechanical properties are also reduced. The effect of alkaline and acid treatments on the biological properties of the material has not been well understood thus far. In the present study, methods are outlined that essentially target nucleic acids alone without affecting the biological, biochemical or mechanical properties of the ECM.

Example 6

Further Characterization of Tissue Processing and Decellularization

To further clarify the steps for decellularization, the following experiment was performed. Small intestine submucosa tissue layer was harvested from the small intestines of market-weight pigs at a slaughterhouse using standard industry practices. The harvested SIS was frozen for transport, received, and stored at −80° C. for later processing. On the day of processing, the 50 to 80 inch long SIS tube was thawed, slit open into a strip, despouged (to remove extraneous material/weakly adhering tissue) and processed in cleaning and disinfection tanks as follows:

(i) an initial rinse in reverse osmosis (RO) water with mechanical agitation for 45 minutes at room temperature, followed by (ii) a first peracetic acid (PAA) rinse (0.15% PAA in 20% ethyl alcohol) with mechanical agitation for 1 hour at room temperature, followed by (iii) a second PAA rinse (0.15% PAA in 20% ethyl alcohol) with mechanical agitation for 1 hour at room temperature, followed by (iv) a reverse osmosis (RO) water rinse with mechanical agitation for 1 hour at room temperature.

At this point, SIS material strips designated for making DePuy Orthopaedics' Restore® implants were removed from the cleaning and disinfection tanks.

To obtain SIS material with further reduced cellular and nuclear debris the following additional processing steps were performed:

(i) a peroxide rinse (3% $H_2O_2$ in RO water) with mechanical agitation for 1 hour at room temp, followed by (ii) a RO water rinse with mechanical agitation for 1 hour at room temperature.

Example 7

Mechanical Testing

In order to test the mechanical strength of the treated SIS, the cleaned and disinfected SIS strips obtained in Example 6 were cut into approximately 4"×4" swatches. Ten swatches were layered onto each other to produce a "device." Several 10-layered, isotropic, laminated devices were dried on gel dryer beds (Model FB-GD-45, Fisher Scientific, Pittsburgh, Pa.) at 30° C. under vacuum. Circular 2.5" diameter devices were cut out after drying, individually packaged, sterilized using electron-beam irradiation, and stored at 2-8° C. for later testing.

To determine whether the additional peroxide rinse effects the mechanical properties of the SIS material, twenty-five Restore® implants and twenty-five peroxide-rinsed SIS implants were tested for mechanical strength using a ball burst test (Whitson et al., (1998) *J Biomed Mater Res*, 43:277-281).

Figure 8:
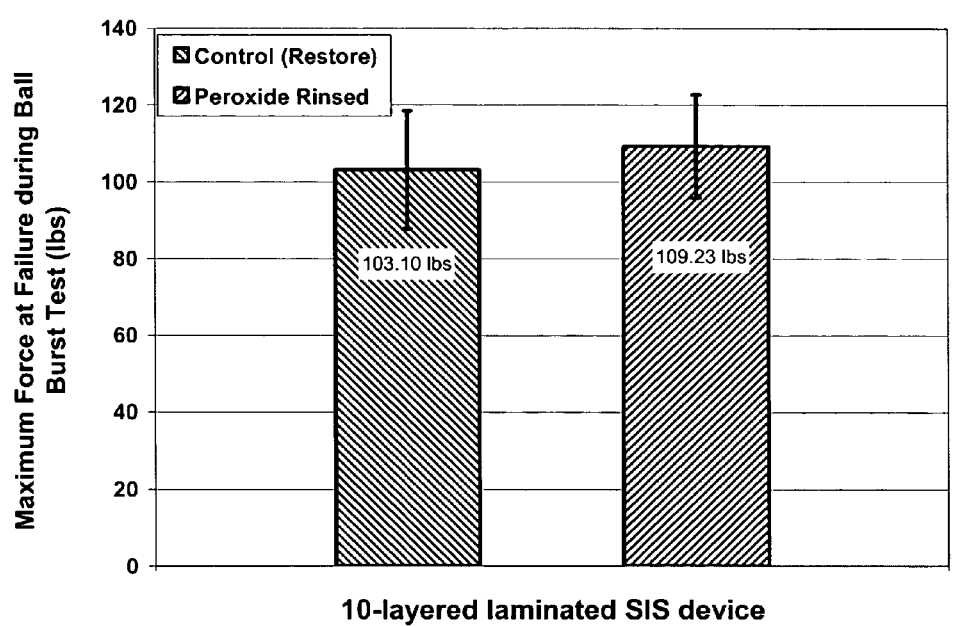
FIG. 8 is a bar graph showing the mechanical testing of the treated SIS.

The results show that the additional peroxide rinse did not adversely effect the mechanical properties of the SIS material. FIG. 8 is a bar graph showing the results of the maximum force at failure during ball burst testing of 10-layered, isotropic, SIS laminate devices. Testing indicated that the ball burst strength of the peroxide-rinsed laminates was somewhat higher (~6% increase) than Restore® samples. There is no significant difference between control (Restore®) and peroxide-treated SIS material (p=0.138).

Example 8

Biological Testing

To determine whether the additional peroxide-rinse affects the biological properties of the SIS material, in vitro cell culture was performed using peroxide-rinsed SIS devices as the substrate for cell growth. Using standard tissue culture procedures, human microvascular endothelial cells (HMEC) were seeded on peroxide-rinsed devices fabricated as described in Example 6. After 5 days of culture the cell-seeded SIS devices were fixed in 10% formaldehyde and processed for histology to visualize cell growth on surface.

Figure 9:
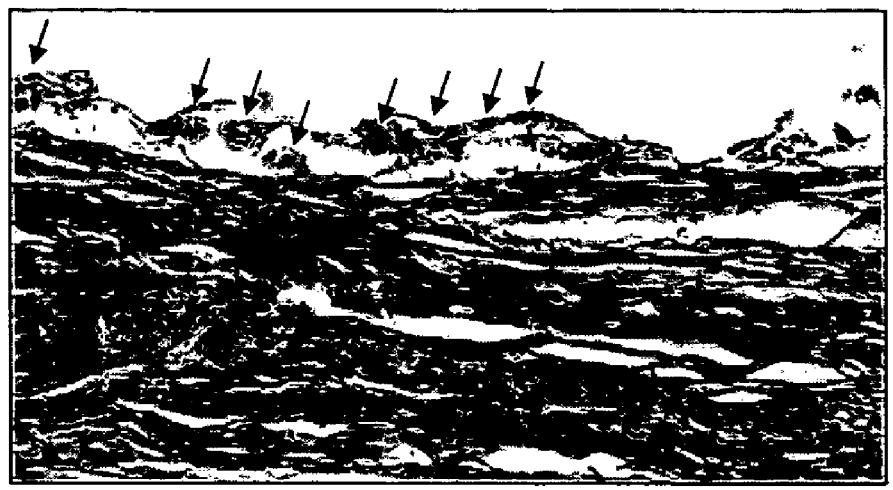
FIG. 9A and FIG. 9B are photographs showing the growth of human microvascular endothelial cells on peroxide rinsed SIS devices.
Figure 9:

The results show that peroxide-rinsed SIS devices supported robust growth of HMECs. The cells adhered well to the surface of the device and were undergoing proliferation. Photomicrographs (FIGS. 9A and 9B) show HMECs adhering and growing on a peroxide-rinsed SIS device (denoted by arrows). These results demonstrate that the additional SIS processing step does not adversely effect the biological properties of the SIS.

The data presented herein demonstrates that additional processing steps of SIS leads to a product that is mechanically, functionally, and biologically similar to the untreated SIS.

The method of the present invention provides a simple, effective process for removing DNA content from a tissue without destroying the complex three-dimensional interstitial structure of the tissue, or without affecting the biochemical and mechanical properties of the ECM.

What is claimed is:

1. A method of decellularizing a tissue by sequential extraction, comprising:

treating isolated tissue with a first solubilizing fluid comprising at least one oxidizing agent at a concentration effective to extract cellular and nuclear material from the tissue, the first solubilizing fluid further comprising at least one of a reactive hydroxyl radical generating agent and a reactive oxygen generating specie;

treating the isolated tissue with a second solubilizing fluid before treating the isolated tissue with the first solubilizing fluid, the second solubilizing fluid comprising at least one oxidizing agent, to remove cellular and nuclear material from the isolated tissue, the at least one oxidizing agent of the second solubilizing fluid being different than the at least one oxidizing agent of the first solubilizing fluid, the second solubilizing fluid further comprising a peroxy acid; and washing the isolated tissue in a washing fluid to remove cellular debris, the method substantially maintaining the biochemical composition and the mechanical and biological properties of an extracellular matrix of the isolated tissue, the method resulting in the extracellular matrix of the tissue being at least about 60% substantially free of viable and non-viable nucleic acids.

2. The method of claim 1, wherein the oxidizing agent in the first solubilizing fluid is selected from the group consisting of hydrogen peroxide, benzoyl peroxide, and t-butyl hydroperoxide.

3. The method of claim 2, wherein the oxidizing agent in the second solubilizing fluid is a peroxy acid selected from the group consisting of peracetic acid, perpropionic acid, perbenzoic acid, diperoxyphthalic acid and peroxyhexanoic acid.

4. The method of claim 1, wherein the oxidizing agent in the first solubilizing fluid comprises hydrogen peroxide.

5. The method of claim 4, wherein the oxidizing agent in the second solubilizing fluid comprises peracetic acid.

6. The method of claim 1, wherein the oxidizing agent in the second solubilizing fluid is a peroxy acid selected from the group consisting of peracetic acid, perpropionic acid, perbenzoic acid, diperoxyphthalic acid and peroxyhexanoic acid.

7. The method of claim 1, wherein the oxidizing agent in the second solubilizing fluid comprises peracetic acid.

8. The method of claim 1, wherein the washing solution is selected from the group consisting of distilled water, physiological buffer and culture medium.

9. The method of claim 1, wherein the first solubilizing fluid further comprises a combination of oxidizing agents.

10. The method of claim 9, wherein the combination comprises hydrogen peroxide and peracetic acid.

11. The method of claim 1, wherein the second solubilizing fluid further comprises a combination of oxidizing agents.

12. The method of claim 11, wherein the combination comprises hydrogen peroxide and peracetic acid.

13. The method of claim 1, further comprising equilibrating the decellularized tissue in equilibrating fluid.

14. The method of claim 1, wherein the decellularized tissue is further dehydrated.

15. The method of claim 1, wherein the extracellular matrix of tissue comprises small intestine submucosa.

16. The method of claim 1, wherein the method results in the extracellular matrix of the tissue being at least about 80% substantially free of viable and non-viable nucleic acids.

17. The method of claim 1, wherein the method results in the extracellular matrix of the tissue being at least about 95% substantially free of viable and non-viable nucleic acids.

18. The method of claim 1, wherein the method results in the extracellular matrix of the tissue being at least about 70% substantially free of viable and non-viable nucleic acids.

19. The method of claim 1, wherein the method results in the extracellular matrix of the tissue being at least about 90% substantially free of viable and non-viable nucleic acids.

20. The method of claim 1, wherein the method results in the extracellular matrix of the tissue being at least about 100% substantially free of viable and non-viable nucleic acids.

21. The method of claim 1, wherein the method results in the extracellular matrix of the tissue having a viable and non-viable nucleic acid content in a range of about 0.5 micrograms/mg to about 50 micrograms/mg.

22. The method of claim 1, wherein the method results in the extracellular matrix of the tissue having a viable and non-viable nucleic acid content in a range of about 3.5 micrograms/mg to about 35 micrograms/mg.

23. The method of claim 1, wherein the method results in the extracellular matrix of the tissue having a viable and non-viable nucleic acid content in a range of about 0.2 micrograms/mg to about 20 micrograms/mg.

24. The method of claim 1, wherein the method results in the extracellular matrix of the tissue having a viable and non-viable nucleic acid content in a range of about 0.1 micrograms/mg to about 10 micrograms/mg.

* * * * *